(12) United States Patent
Tanaka

(10) Patent No.: US 8,352,016 B2
(45) Date of Patent: Jan. 8, 2013

(54) DATA COLLECTION FOR ELECTRICAL IMPEDANCE TOMOGRAPHY

(75) Inventor: Harki Tanaka, Sào Paulo (BR)

(73) Assignee: Timpel S.A., Sao Paulo (BR)

(*) Notice: Subject to any disclaimer, the term of this patent is extended or adjusted under 35 U.S.C. 154(b) by 66 days.

(21) Appl. No.: 12/383,604

(22) Filed: Mar. 27, 2009

(65) Prior Publication Data
US 2009/0234244 A1 Sep. 17, 2009

Related U.S. Application Data

(63) Continuation of application No. PCT/IB2007/003726, filed on Aug. 28, 2007.

(30) Foreign Application Priority Data

Aug. 28, 2006 (BR) ...................................... 0604484

(51) Int. Cl.
A61B 5/00 (2006.01)
(52) U.S. Cl. .......................... 600/425; 600/547; 324/600
(58) Field of Classification Search .................. 600/407, 600/425, 547; 324/323–326, 347, 354, 600
See application file for complete search history.

(56) References Cited

U.S. PATENT DOCUMENTS

| 4,649,932 | A | * | 3/1987 | Smith | ........................... 600/547 |
| 4,920,490 | A | | 4/1990 | Isaacson | |
| 5,272,624 | A | | 12/1993 | Gisser et al. | |
| 5,311,878 | A | | 5/1994 | Brown et al. | |
| 5,381,333 | A | | 1/1995 | Isaacson et al. | |
| 5,626,146 | A | | 5/1997 | Barber et al. | |
| 6,784,672 | B2 | * | 8/2004 | Steele et al. | ................... 324/663 |
| 7,514,921 | B2 | * | 4/2009 | Woo et al. | ...................... 324/300 |
| 7,603,158 | B2 | * | 10/2009 | Nachman et al. | ............. 600/411 |

(Continued)

FOREIGN PATENT DOCUMENTS
WO WO 03/043493 A2 5/2003

OTHER PUBLICATIONS

Jaakko Malmivuo et al., "Web-Version: Bioelectromagnetism—Principles and Applications of Bioelectric and Biomagnetic Fields" 1195, Oxford University Press, New York, XP002479937.

(Continued)

Primary Examiner — Brian Casler
Assistant Examiner — Amanda Lauritzen
(74) Attorney, Agent, or Firm — Shlesinger, Arkwright, & Garvey LLP

(57) ABSTRACT

The invention refers to a method for carrying out data collection on electrodes placed on a body for subsequent processing of an electrical impedance tomography image of a corresponding part of said body. In order to improve the resolution of electrical impedance tomography systems without noticeably affecting the signal-to-noise ratio, the method according to the invention comprises the steps of placing the electrodes on a peripheral line around the body, applying a current pattern from a current source to at least one pair of electrodes, and measuring differential potentials between pairs of electrodes, wherein at least one intermediate electrode lies in between each pair of electrodes for measuring the differential potentials and the differential potentials of one current pattern for the subsequent image processing refer to at least three different pairs of electrodes with no electrode used more than twice for each current pattern.

18 Claims, 13 Drawing Sheets

U.S. PATENT DOCUMENTS

| | | | | |
|---|---|---|---|---|
| 7,865,236 B2 * | 1/2011 | Cory et al. | ............... | 600/547 |
| 7,941,210 B2 * | 5/2011 | Matthiessen et al. | ......... | 600/547 |
| 2005/0107834 A1 * | 5/2005 | Freeman et al. | ............... | 607/5 |
| 2007/0083239 A1 * | 4/2007 | Demarais et al. | ............... | 607/2 |

OTHER PUBLICATIONS

International Search Report of May 28, 2008.

Hua, P. et al.: "Effect of the measurement method on noise handling and imgae quality of EIT imaging", Proceedings of the Ninth Annual Conference of the IEEE.

Engineering in Medicine and Biology Society, New York, NY, USA, vol. 3 of 4 vol. xciv+2125 pp. 1429-1430, 1987.

Woo, E.J. et al.: "Measuring Lung Resistivity Using Electrical Impedance Tomography", IEEE Transactions on Biomedical Engineering, vol. 39, No. 7, p. 756-760, Jul. 1992.

Hua, P. et al.: "Finite Element Modeling of Electrode—Skin Contact Impedance in Electrical Impedance Tomography". IEEE Transactions on Biomedical Engineering, vol. 40, p. 335-343, Apr. 1993.

Avis, N.J. et al.: "Image reconstruction using non-adjacent drive configurations", Physiological Measurement, vol. 15, A153-A160, 1994.

Santosa F. et al.: "A backprojection algorithm for electrical impedance imaging", SIAM, 50: 216-243, 1990.

Morucci J.P. et al.: "A direct sensitivity matrixx approach for fast reconstruction in electrical impedance tomography", Physiological Measurement, 15:A104-A114, 1994.

* cited by examiner

DATA COLLECTION FOR ELECTRICAL IMPEDANCE TOMOGRAPHY

RELATED APPLICATIONS

This is a continuation application of International PCT Application No. PCT/IB2007/003726, with an international filing date of Aug. 28, 2007, claiming the priority benefit of Brazil Patent Application No. PI 0604484-0, filed on Aug. 28, 2006, hereby incorporated by reference.

The invention refers to a method for carrying out data collection on electrodes placed on a body for subsequent processing of an electrical impedance tomography image of a corresponding part of said body.

Electrical impedance tomography (EIT) is an imaging method of a volume conductor of interest, e.g. the thorax of a human body. When applying electrical impedance tomography to a thorax, a number of electrodes are placed around the thorax wherein an alternating current with e.g. 50 kHz at 5 mA peak to peak amplitude is applied via a pair of (preferably adjacent) electrodes. The other electrodes are used to carry out the measurements of the voltages against a defined reference potential resulting from the applied current. The pair of electrodes for applying the current consists of a driving electrode, i.e. positive pole, and a sinking electrode, i.e. negative pole. As soon as all the electrodes have served as driving electrodes, a cycle for data collection is concluded. Each different choice of current applying electrodes will produce a different so-called current pattern. In order to eliminate statistical disturbances, a plurality of data collection cycles may be averaged. The special feature of electrical impedance tomography is that on the basis of a computer-based processing of the signals at the electrodes, a two-dimensional or even three-dimensional image of the impedance distribution and of the impedance changes can be compiled.

Different methods are known to carry out the data collection on the electrodes.

From U.S. Pat. No. 5,311,878 it is known to apply current through neighbouring electrodes and to measure the voltage successively from all other adjacent electrode pairs.

From U.S. Pat. No. 4,920,490 and U.S. Pat. No. 5,381,333 it is known to apply current through a plurality of electrodes simultaneously, wherein the voltages of the electrodes are measured with respect to a single grounded electrode.

From U.S. Pat. No. 5,272,624 it is known to apply current through a plurality of electrodes simultaneously, wherein the voltages of the electrodes are measured with respect to a common ground.

From Hua, P., Webster, J. G., Tompkins, W. J.: "Effect of the measurement method on noise handling and image quality of EIT imaging", Proceedings of the Ninth Annual Conference of the IEEE Engineering in Medicine and Biology Society, New York, N.Y., USA, vol. 3 of 4 vol.xciv+2125 pp., p. 1429-30, 1987, it is known to apply a current using a pair of more distant electrodes and to measure the resulting voltages successively for all remaining adjacent electrode pairs. It is also mentioned that the current may be applied through two diametrically opposed electrodes.

From Woo, E. J., et al.: "Measuring Lung Resistivity Using Electrical Impedance Tomography", IEEE Transactions on Biomedical Engineering, vol. 39, no. 7, p. 756-760, July 1992, it is known to apply current using an optimal current pattern and to measure the resulting boundary voltages with respect to a common reference.

From Hua, P., et al.: "Finite Element Modeling of Electrode-Skin Contact Impedance in Electrical Impedance Tomography", IEEE Transactions on Biomedical Engineering, vol. 40, no. 4, p. 335-343, April 1993, it is known to apply current through neighbouring electrodes and to measure the resulting voltages with respect to a common reference electrode.

From Avis, N. J., Barber, D. C.: "Image reconstruction using non-adjacent drive configurations", Physiological Measurement, vol. 15, A153-A160, 1994, it is known to apply current between electrodes in the adjacent, cross and polar configuration and to measure the resulting voltages of non-current carrying adjacent electrode pairs.

Spatial resolution and noise are the most important constraints in possible clinical applications. Spatial resolution is limited by the number of independent measurements that can be made from a given number of electrodes. It follows that if the number of electrodes used is increased, then the spatial resolution might be improved. If the number of electrodes is doubled, then the number of independent measurements will quadruple and the spatial resolution could be improved by a factor of two. However, increasing the number of electrodes also reduces the signal-to-noise ratio. Furthermore, the resolution is also limited by a three-dimensional spread of the current, so that the improvement in resolution cannot be increased continuously by increasing the number of electrodes.

It is an object of the invention to provide a method for an electrical impedance tomography system by which the resolution can be improved without noticeably affecting the signal-to-noise ratio.

This object is solved by a method according to claim 1.

The method according to the invention comprises the steps of placing the electrodes on a peripheral line around the body, applying a current pattern from a current source to at least one pair of electrodes, and measuring differential potentials between pairs of electrodes, wherein at least one intermediate electrode lies in between each pair of electrodes for measuring the differential potentials and the differential potentials of one current pattern for the subsequent image processing refer to at least three different pairs of electrodes with no electrode used more than twice for each current pattern.

If the potentials of both electrodes of an electrode pair are known, it will be possible to determine the voltage between said electrodes by calculating the difference between both potentials. In the sense of the invention the differential potential of said pair of electrodes is equivalent to this voltage between the electrodes.

The basic cognition of the invention is the fact that the signal-to-noise ratio can be improved if the distance between a pair of electrodes for a measurement of the differential potential is increased. Hence, rather than using adjacent pairs of electrodes for measuring the differential potentials, the invention suggests to use one of the electrodes after the next electrode for measuring the differential potential. At the same time, all possible combinations of pairs of electrodes on said peripheral line could still be used for one current pattern if an overlapping pattern of measurement pairs is applied for each current pattern.

One further advantage of the method according to the invention is related to the dynamic range of differential potentials, i.e. the ratio between the highest and the lowest differential potential. It can be noted that a decrease of the dynamic range improves also the quality of the digital demodulation process.

As an illustration of the advantages outlined above, a theoretical experiment with a 64-electrode configuration and with a 32-electrode configuration was performed employing a finite element model, where the electronic white noise commonly observed in currently available devices for electrical impedance tomography was simulated (around 20 μV per channel). When simulating a configuration with adjacent electrode pairs (adjacent configuration), the image quality of a 64-electrode adjacent configuration was worse compared to a 32-electrode adjacent configuration, despite the much greater number of independent measurements. However, when simulating a 64-electrode configuration with 1 electrode positioned in between the pairs of electrodes, the image quality of this 64-electrode configuration was clearly superior compared to the 32-electrode adjacent configuration.

When compared to systems using adjacent electrode pairs for voltage measurements, the proposed configuration resulted in a fourfold increase in voltage signals at the opposite side in the body with respect to the current application position. Consequently, the signal-to-noise ratio improved by the same amount and the image noise could be reduced considerably. Furthermore, the proposed configuration decreased the dynamic range twofold which resulted in an improvement of the quality of the digital demodulation process.

According to one aspect of the invention the at least one intermediate electrode is part of another pair of electrodes for measuring the differential potentials. This aspect of the invention results in an interleaved configuration of the pairs of measurement electrodes. This can be accounted for in the subsequent processing of an electrical impedance tomography image of the body. With a simple adaptation, any algorithm can incorporate the spatially overlapping voltage information generated by the proposed configuration during each specific current pattern.

It should be noted, however, that not only the distance of the measuring pairs of electrodes can be increased by skipping electrodes in between, but that the same can be applied to the pairs of electrodes for applying a current. Increasing the distance of the electrodes applying a current increases the current density in the opposite side of the body, since the shunt of current across tissue interposed between the electrodes applying the current decreases.

When choosing the number of electrodes lying in between current applying pairs and measuring pairs of electrodes the trade-off between spatial resolution and signal-to-noise ratio has to be considered. The best number of interposed electrodes depends on the system noise as well as on the dimensions of the body to be measured. Principally, the number of electrodes lying in between the pairs of electrodes can be different for current applying pairs versus measuring pairs but most configurations will result in the same number of interposed electrodes used for current applying pairs and measuring pairs.

Hence, according to another aspect of the invention the same number of electrodes lies in between each pair of electrodes for measuring a differential potential. This kind of configuration has the advantage that there is a regular pattern of the pairs of electrodes for measuring the differential potentials which simplifies the subsequent processing of the electrical impedance tomography image. The optimum number of electrodes between said pairs of electrodes for obtaining the best trade-off between spatial resolution and signal-to-noise ratio depends on the spatial dimensions of the whole configuration. On the other hand, the spatial dimensions (i.e. in particular the distance between the electrodes which are placed on the peripheral line around the body) can be chosen such that the best result is obtained if always exactly one electrode lies in between said pairs of electrodes for measuring the differential potentials.

According to another aspect of the invention the same number of electrodes lies in between each pair of electrodes for applying a current. This kind of configuration has the same advantage as described above with regard to the pairs of electrodes for measuring the differential potentials, i.e. the resulting current patterns are similar to each other which simplifies the subsequent processing of the electrical impedance tomography image. However, in contrast to the pairs of electrodes for measuring the differential potentials, the distance between the pairs of electrodes for applying a current does not influence in the first place the signal-to-noise ratio of the measurement. Rather, there is a further criterion for choosing the optimum number of electrodes between the pairs of electrodes for applying a current which is the resulting number of independent data collection measurements for all possible current patterns. Monte-Carlo simulations which have been carried out in this regard suggest that the maximum number of independent measurements can be obtained when the number of interleaved electrodes is equal both for the pairs of electrodes for measuring the differential potentials and for the pairs of electrodes for applying a current. However, the benefit between the maximum and the next best combination according to the Monte-Carlo simulations was not substantial, namely just one additional measurement.

According to another aspect of the invention for one current pattern each electrode on said peripheral line is used either for applying a current or for measuring differential potentials. The advantage of excluding the electrodes for applying a current from measuring differential potentials is the fact that the contamination of the reading voltage by the contact impedance (electrode-skin) can be avoided. By having no current, the potentials in the skin and at the electrode will be in close equilibrium. However, by having some current passing through the electrode, the potential at the skin will be always different from the potential generated at the electrode metal. Having a 32-electrode configuration, there are still 28 independent differential voltage measurements for each current pattern if the electrodes for applying a current are excluded. Even considering the redundancy caused by the reciprocity principle, this configuration results in approximately the same amount of independent information as in the adjacent configuration. Therefore, resolution is minimally affected while the signal-to-noise ratio improves 3 to 4 times.

According to another aspect of the invention for one current pattern each electrode on said peripheral line is used for measuring differential potentials. Preferably, for one current pattern each electrode is used twice for measuring differential potentials. In this way the maximum information possible will be obtained from the given number of electrodes. Hence, the number of differential potential measurements is equal to the number of electrodes. Consequently, this requires that the electrodes for applying a current also are used for the differential potential measurements, wherein in this configuration the influence of the current application has to be taken into account with regard to the differential potential measurement.

According to another aspect of the invention a differential potential measurement is performed by measuring a first voltage of a first electrode with regard to the ground of the current source, measuring a second voltage of a second electrode with regard to the ground of the current source and subtracting the second voltage from the first voltage. This measurement of differential potentials between pairs of electrodes always ensures that the existing noise against the reference potential is compensated as far as possible. This is to be explained by the fact that noise components against the reference potential which are equally present on both electrodes are suppressed if the differential potential between both electrodes is measured by a differential amplifier. Hence, the major source of noise results then merely from the differential amplifiers themselves employed in differential potential measurements, which commonly produce some background noise with nearly constant amplitude depending on the common-mode rejection and the environment. Consequently, any increment in the amplitude of differential potentials in electrode pairs as proposed according to the invention results in an immediate improvement of the signal-to-noise ratio.

According to another aspect of the invention a balanced current source is used having the mid-point earthing as ground. The advantage of this configuration is the fact that no reference electrode is needed for the ground potential. Instead, the mid-point earthing of the current source can serve as a reference potential.

According to another aspect of the invention the electrodes are placed on at least one electrode unit. An electrode unit combines a number of electrodes into one element which can be applied to the patient's body. Either an electrode unit comprises all electrodes required for the measurement, e.g. an electrode belt, or several electrode units, so-called electrode modules, are combined in order to obtain the required number of electrodes. Various configurations of an electrode belt are known, e.g. from WO 03/043493 A2. On the other hand electrode modules are available having e.g. 8 electrodes per module. In this way four modules can be used to perform measurements with 32 electrodes. Advantages of electrode modules are their easier production and easier clinical use.

In the following the present invention will be further explained with reference to the following figures in which:

FIG. 1 shows the adjacent configuration for applying a current and for measuring a differential potential according to the prior art using 16 electrodes, FIG. 2 shows the adjacent configuration for applying a current and for measuring a differential potential according to the prior art using 32 electrodes, FIG. 3 shows a configuration according to the invention for applying a current and for measuring a differential potential employing an electrode belt with 32 electrodes, FIG. 4 shows a detail of a configuration according to the invention with 32 electrodes surrounding a section of the body with homogeneous resistivity, FIG. 5 shows a typical case of differential potential measurements in a tank simulating a human thorax according to the prior art, FIG. 6 shows a typical case of differential potential measurements according to the invention, FIG. 7 shows a comparison of the measurements of differential potential signals between a configuration according to the prior art as shown in FIG. 5 and a configuration according to the invention as shown in FIG. 6, FIG. 8 shows an illustration of a saline tank model and a non-conductive object placed in it to be used within the simulation, FIG. 9 shows the result of an image reconstruction using an adjacent configuration and a back-projection algorithm, FIG. 10 shows the result of an image reconstruction using a configuration according to the invention with one electrode lying in between the current applying pairs/measuring pairs and a back-projection algorithm, FIG. 11 shows the result of an image reconstruction using a configuration according to the invention with three electrodes lying in between the current applying pairs/measuring pairs and a back-projection algorithm, FIG. 12 shows the result of an image reconstruction using an adjacent configuration and a reconstruction algorithm based on the sensitivity matrix calculations for a finite element mesh model, and FIG. 13 shows the result of an image reconstruction using a configuration according to the invention with one electrode lying in between the current applying pairs/measuring pairs and a reconstruction algorithm based on the sensitivity matrix calculations for a finite element mesh model.

FIG. 1 shows the adjacent configuration for applying a current and for measuring a differential potential according to the prior art using 16 electrodes. Depicted is a cross-sectional view of a test subject in the plane of an electrode belt. FIG. 1 shows an adjacent configuration for applying a current and for measuring a differential potential. A high output current source is applied across electrodes 1 and 2, while the difference of the potential between other electrode pairs is measured—to simplify matters only the opposite differential potential, i.e. between electrodes 9 and 10, is depicted. The opposite differential potential corresponds usually to the lowest one.

FIG. 2 shows the same configuration as FIG. 1 but illustrates that, when the number of electrodes doubles to 32 electrodes, while keeping the adjacent configuration, the distance between electrodes 1 and 2 shortens, increasing the shunting current through the skin in between these electrodes. As a result, current density decreases in the opposite side of the body, decreasing potential gradients. The distance separating the opposite measurement pair, namely electrodes 17 and 18, becomes also less, decreasing further the potential gradients.

FIG. 3 shows a configuration according to the invention for applying a current and for measuring a differential potential employing an electrode belt with 32 electrodes. One current pattern is depicted, where driving and sinking electrodes are electrodes 1 and 3, respectively. The subsequent current pattern would occur using electrodes 2 and 4 for current application, and so on. Despite the use of 32 electrodes, the measured differential potential gradients are similar to those in FIG. 1. Current density is higher in the opposite side of the body, and the distance within measurement pairs increases. There is some spatial overlapping of information, which can easily be accounted for by the reconstruction algorithm. However, each differential potential is an independent information, and there is much more independent information for the image reconstruction in this configuration than in a 16-electrode configuration. Therefore, the image resolution is better than in FIG. 1, while the signal-to-noise ratio is better than in FIG. 2.

According to a preferred embodiment of the invention all measurements of differential potentials are performed simultaneously. Possible movements of the body and/or changes in the impedance within the body during the measurements are taking place will reduce the quality of the electrical impedance tomography image. It is therefore desirable to reduce the time required for the differential potential measurements for a given current pattern. Performing the differential potential measurements simultaneously leads to the shortest possible measurement time and consequently the best measurement conditions. Furthermore, a single bipolar current source is preferably used to apply the current to each pair of electrodes selected for applying current. This current source with high output impedance is multiplexed among all possible pairs of electrodes. Compared to systems using a current source at each electrode pair employed for applying current, this will further reduce the noise in the system.

FIG. 4 shows a detail of a configuration according to the invention with 32 electrodes surrounding a section of the body with homogeneous resistivity. The electrodes for applying a current are 1 and 3 at the opposite side of the body.

Isopotential lines connecting the dipole formed between electrodes 1 and 3 and electrodes 12 and 14 are depicted. It can be observed that there is some spatial overlap of information carried by the differential potentials measured by amplifiers 16 and 17, respectively, which must be accounted for by the reconstruction algorithm. Any impedance perturbation occurring in the overlapping region will cause a simultaneous change in the differential potentials measured by amplifiers 16 and 17.

Figure 1:
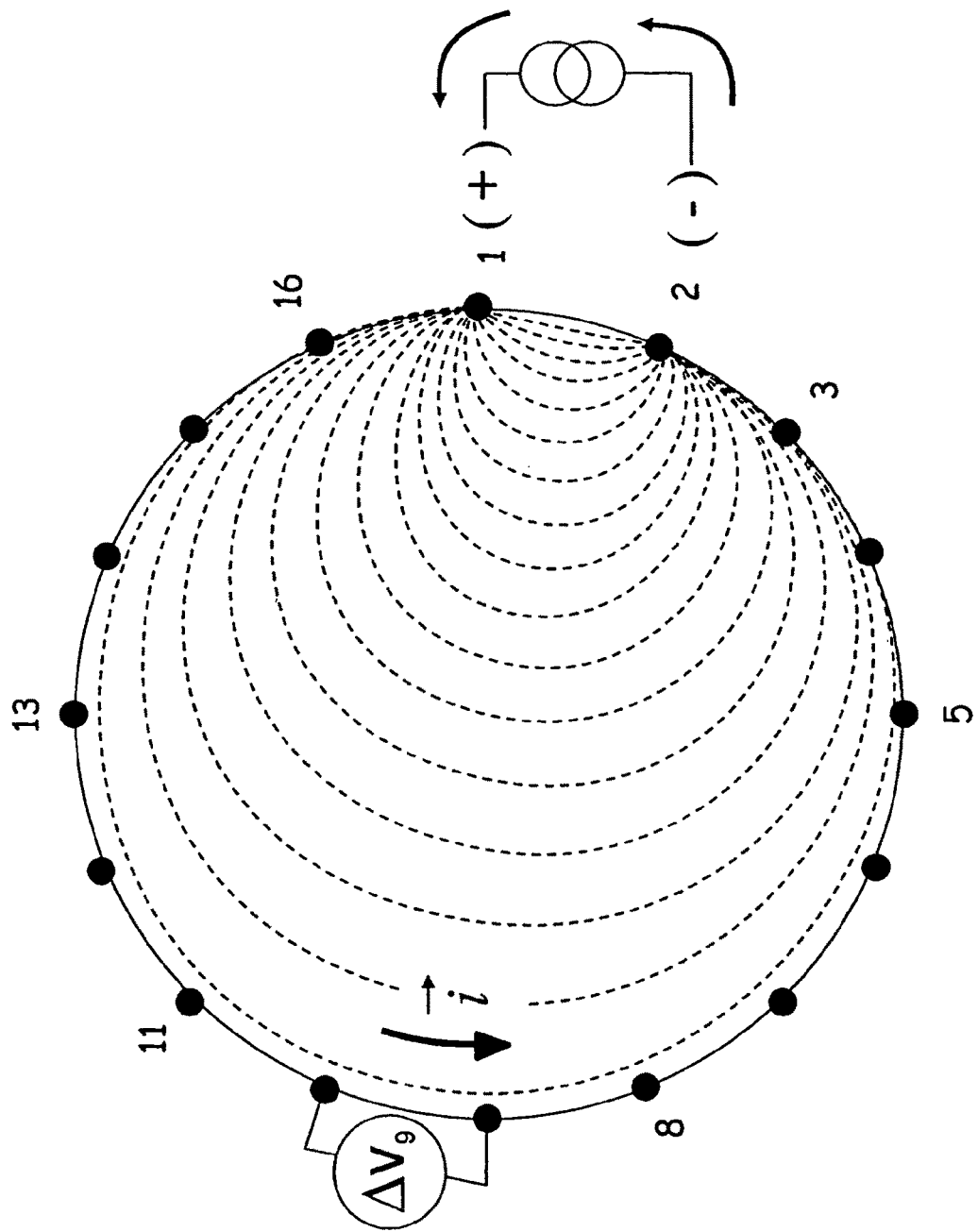
Figure 2:
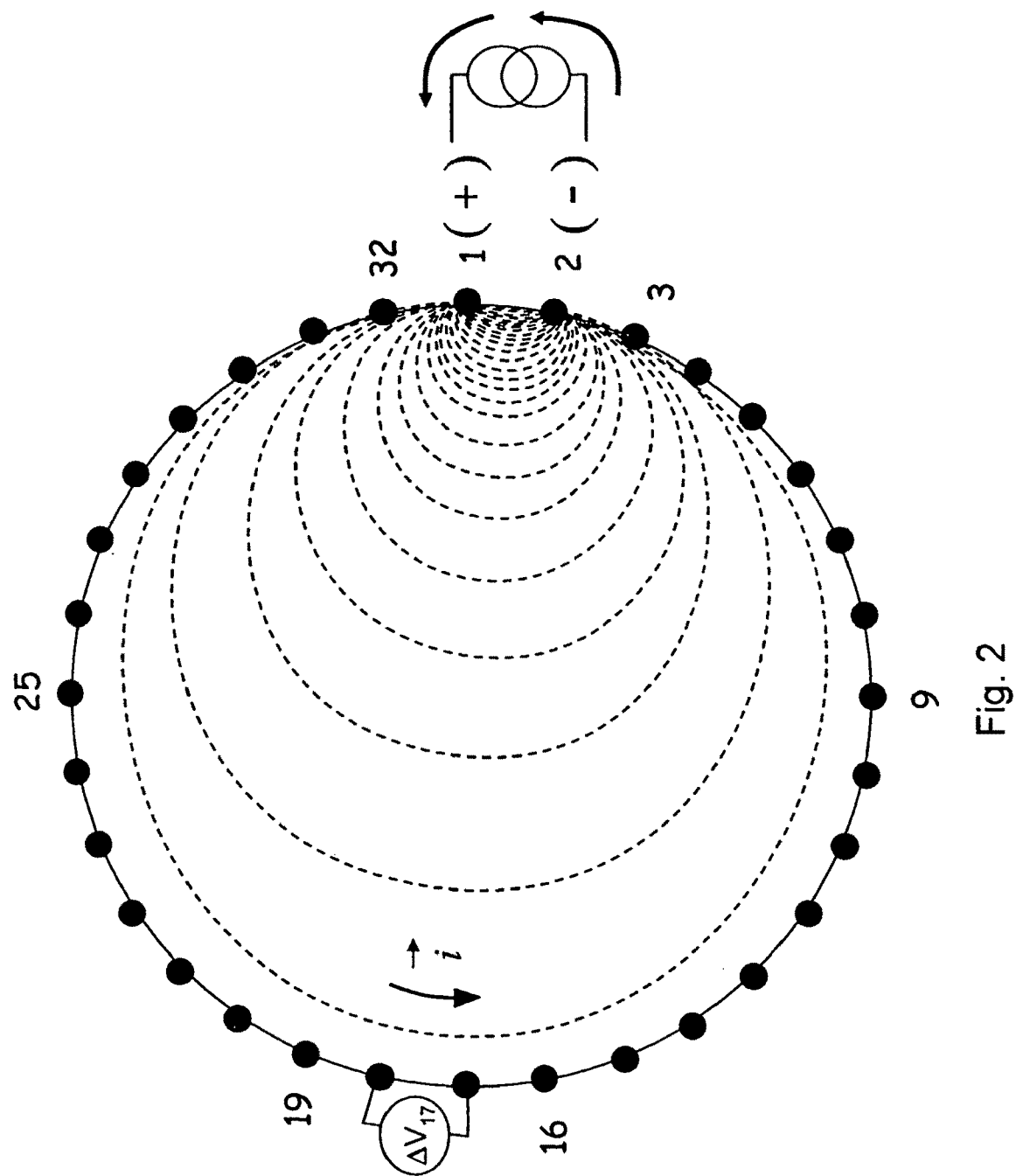
Figure 3:
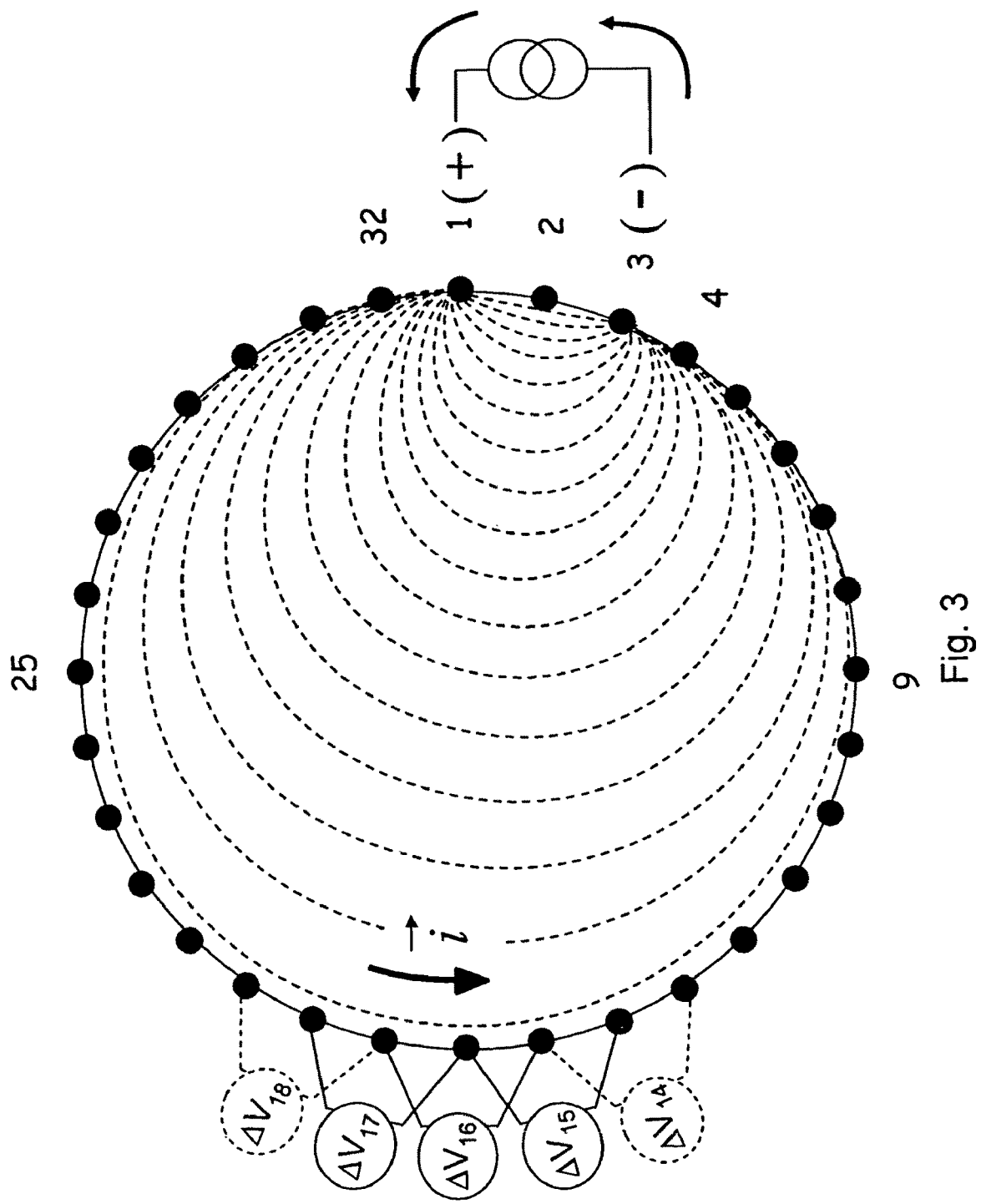
Figure 4:
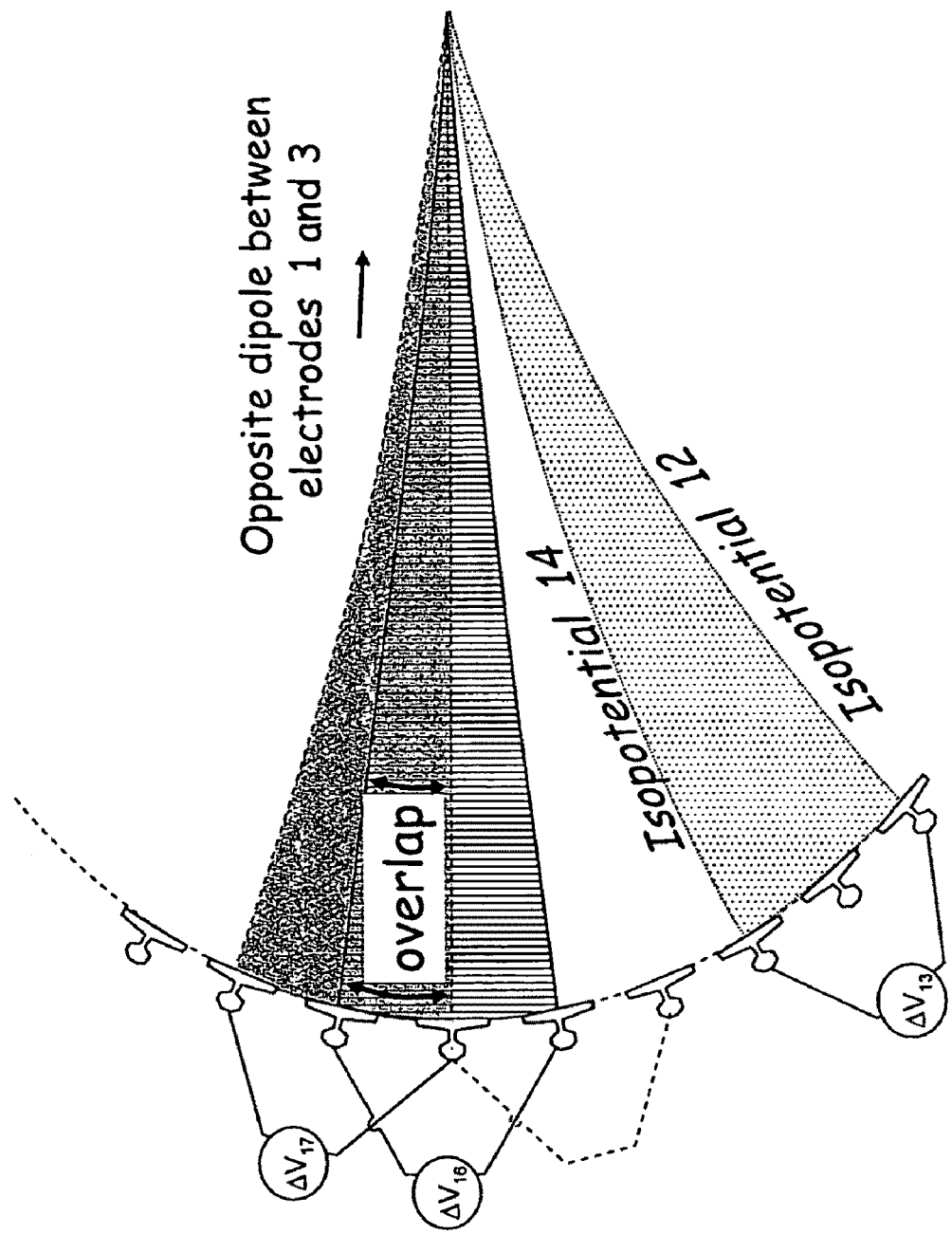
Figure 5:
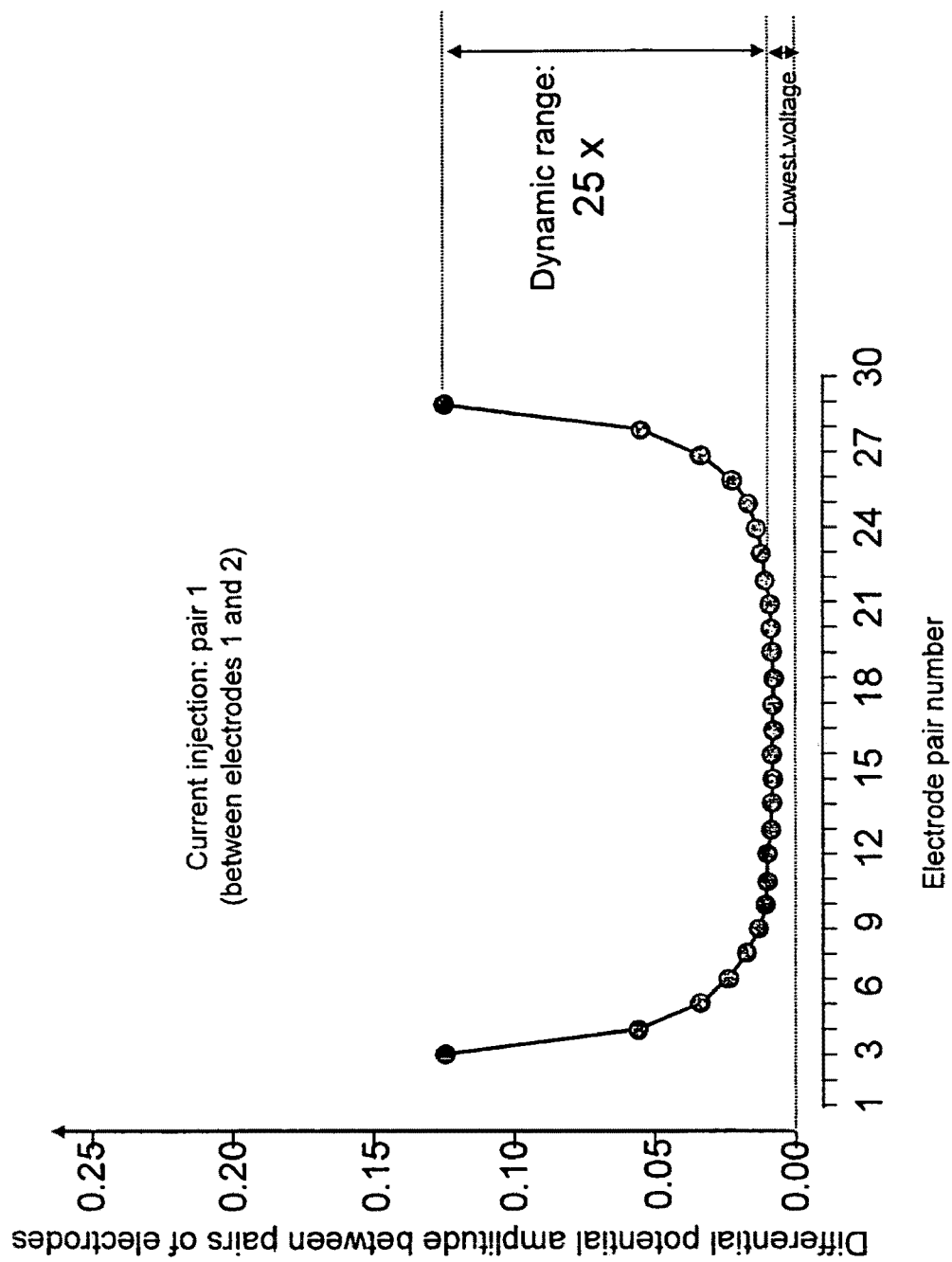
FIG. 5 shows a typical case of differential potential measurements in a tank simulating a human thorax, with a 32-electrode adjacent configuration according to the prior art. To simplify matters, the differential potential measurements corresponding to pairs 32-1, 1-2, and 2-3 are not depicted.
Figure 6:
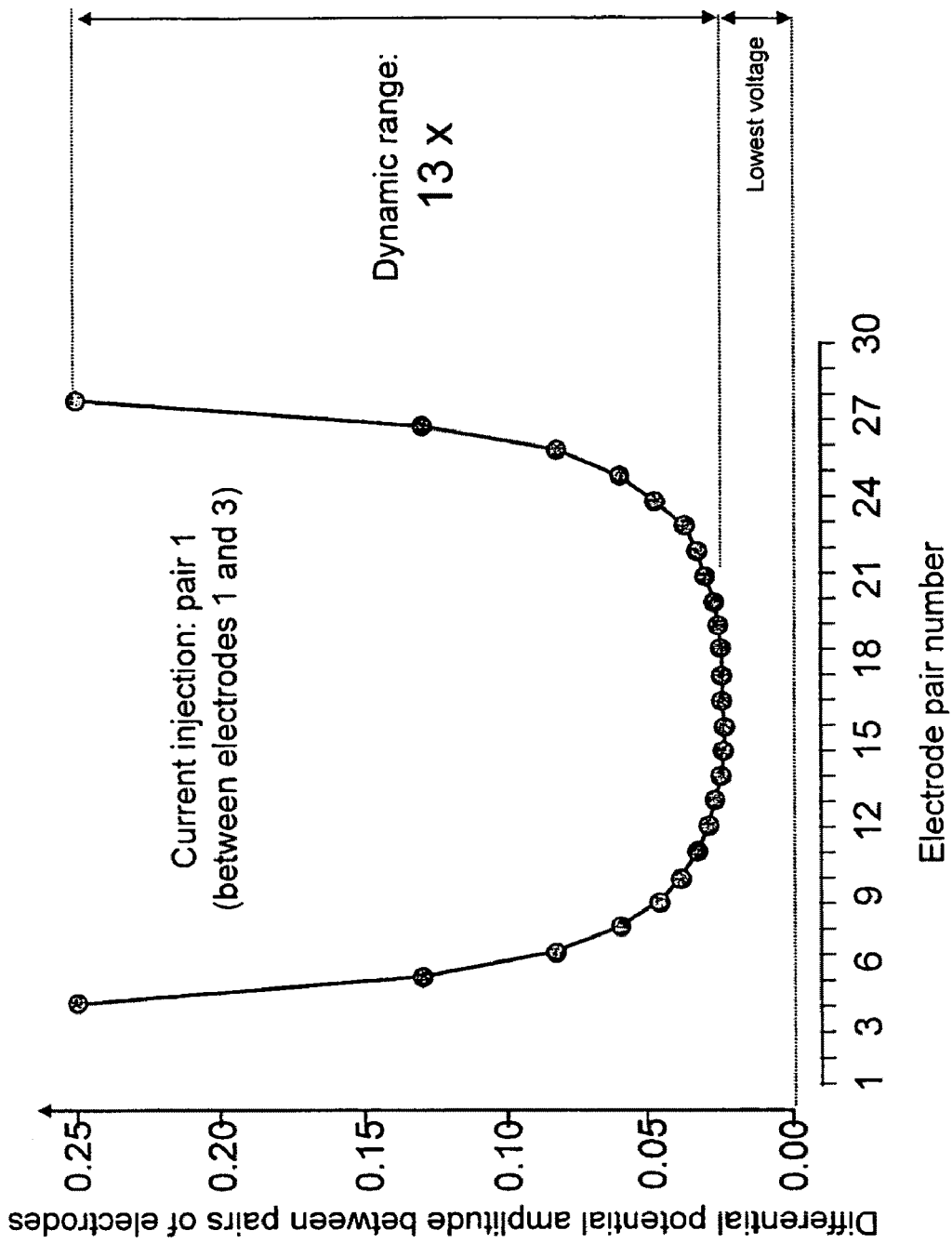
FIG. 6 shows a typical case of differential potential measurements in the same tank as in FIG. 5, with the same current source and intensity, using a 32-electrode configuration according to the invention. To simplify matters, measurements corresponding to electrode pairs 31-1, 32-2, 1-3, 2-4 and 3-5 are not shown.
Figure 7:
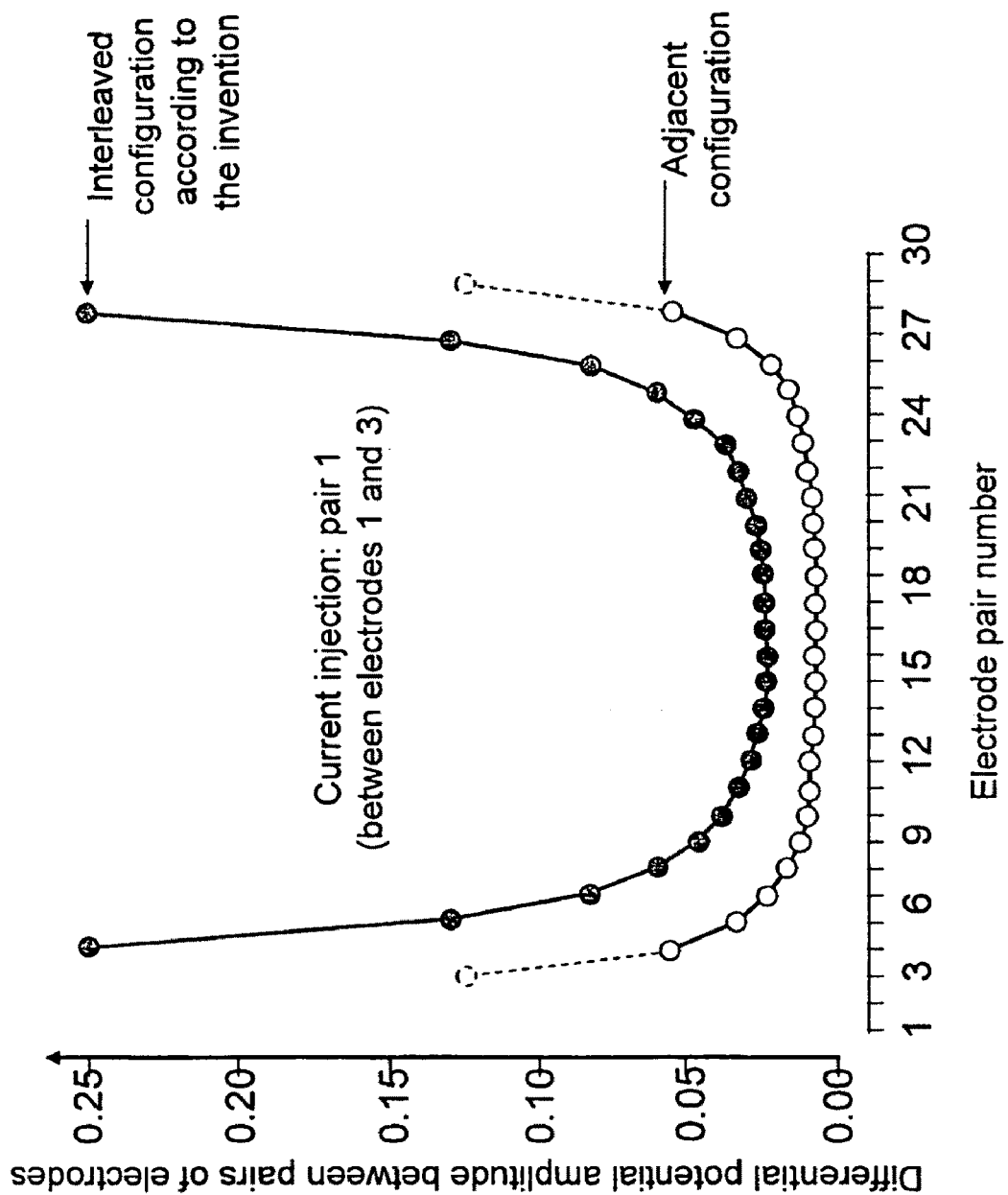

FIG. 7 shows a comparison of the measurements of differential potential signals between a configuration according to the prior art as shown in FIG. 5 and a configuration according to the invention as shown in FIG. 6. FIG. 7 shows the increase in differential potential signals up to fourfold, which usually causes an improvement in the signal-to-noise ratio by the same order of magnitude. One additional advantage of the configuration according to the invention is related to the dynamic range of differential potentials, which decreased almost twofold, potentially improving the quality of the digital demodulation process.

Figure 8:
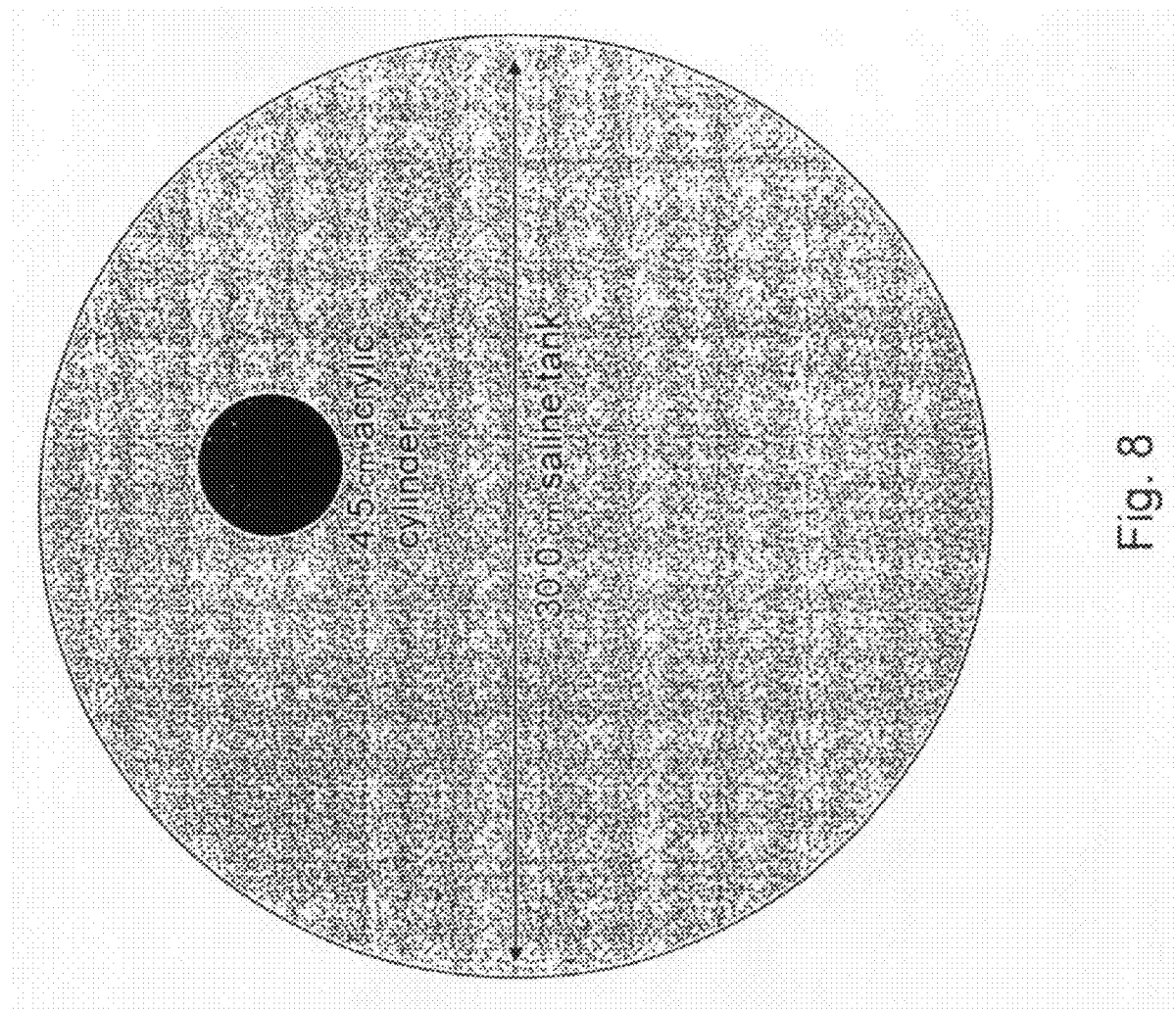

FIG. 8 shows an illustration of a saline tank model and a non-conductive object placed in it to be used within the following simulations. A physiological solution with 0.9% NaCl composition was used and the current source applied 0.1 mA at 125 kHz. This setup resulted in a nearly constant random noise in all channels with a standard deviation of about 0.01 mV. An acrylic cylinder, with 4.5 cm diameter was placed in the position illustrated, that is midway between the centre and the border.

Figure 9:
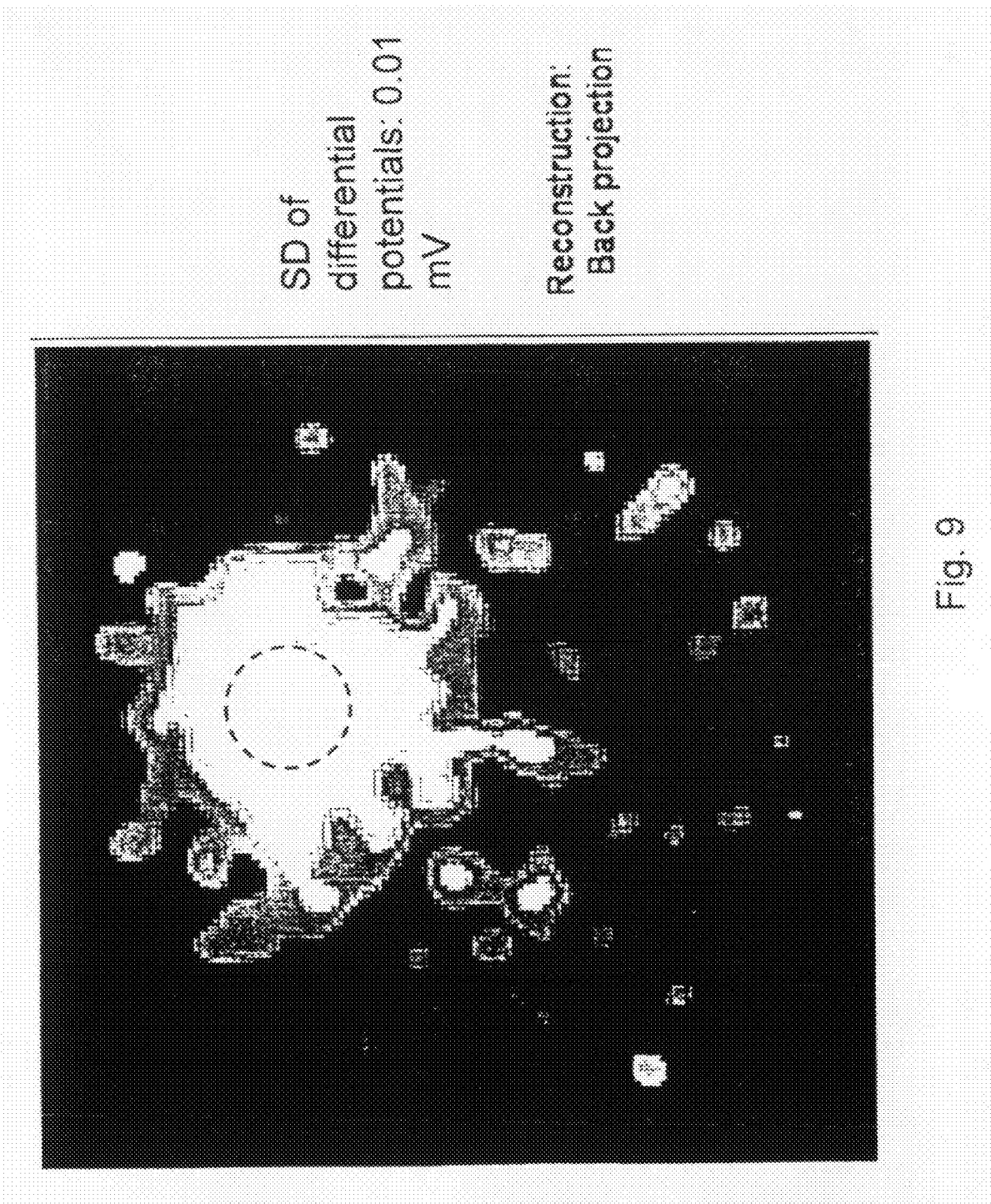

FIG. 9 shows the result of an image reconstruction of the non-conductive object according to FIG. 8 using an adjacent configuration and a back-projection algorithm. The back-projection algorithm is explained for example in Santosa F. and Vogelius M., "A backprojection algorithm for electrical impedance imaging", SIAM, 50: 216-243, 1990. The contour of the original non-conductive object is superposed to illustrate the expected position of the object in the image. The signal-to-noise ratio in the lowest voltages was about 40 dB.

Figure 10:
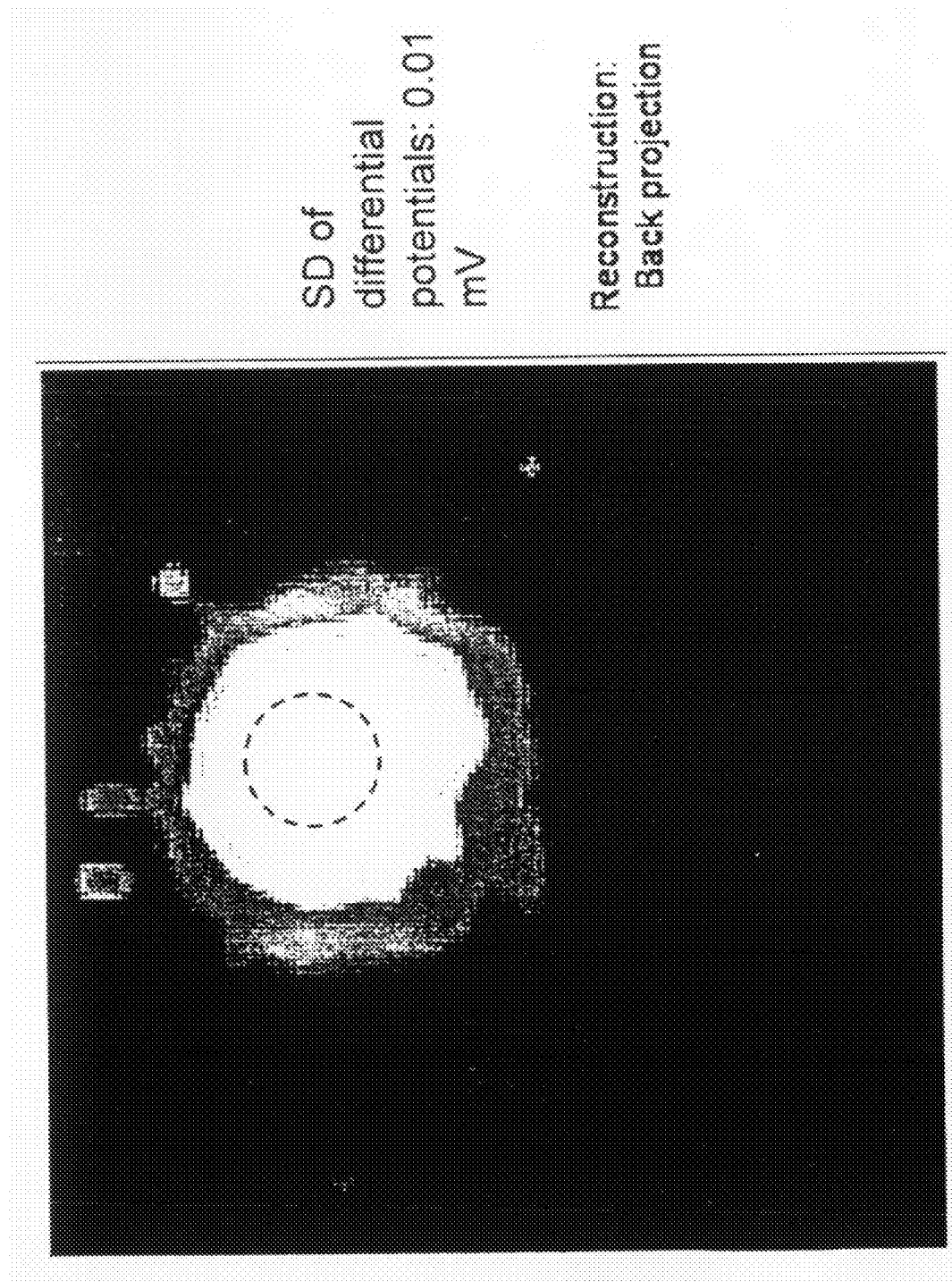

FIG. 10 shows the result of an image reconstruction using a configuration according to the invention with one electrode lying in between the current applying pairs/measuring pairs and a back-projection algorithm. The current source and intensity was the same as in FIG. 9, with the same system and cables, generating exactly the same background noise. The signal-to-noise ratio improved fourfold, with a visible improvement in the image quality.

Figure 11:
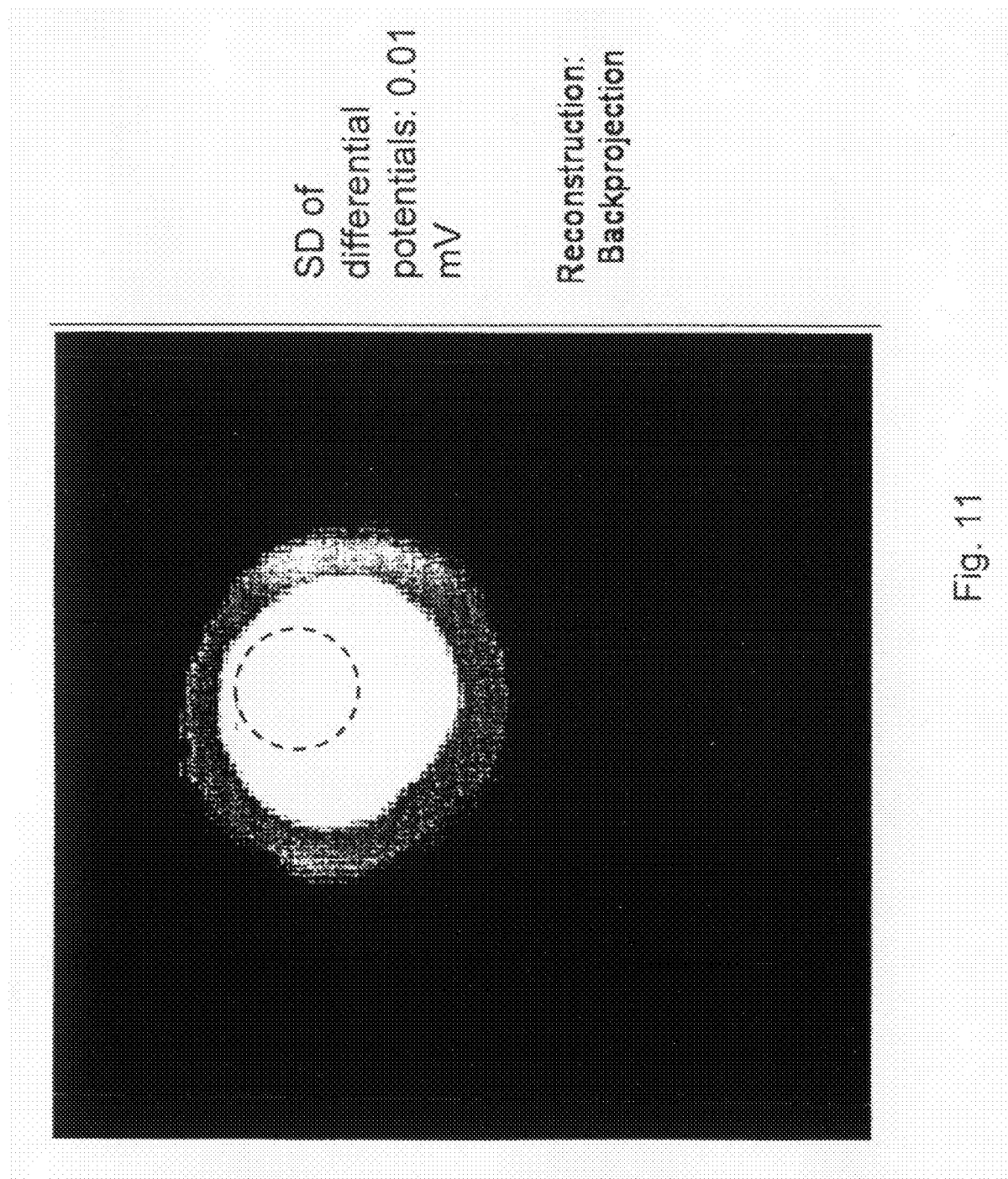

FIG. 11 shows the result of an image reconstruction using a configuration according to the invention with three electrodes lying in between the current applying pairs/measuring pairs and a back-projection algorithm. The current source and intensity was the same as in FIG. 9, with the same system and cables, generating exactly the same background noise. The signal-to-noise ratio improved further, when compared to FIG. 10, but there is already some deterioration in the object positioning and in the resolution.

Figure 12:
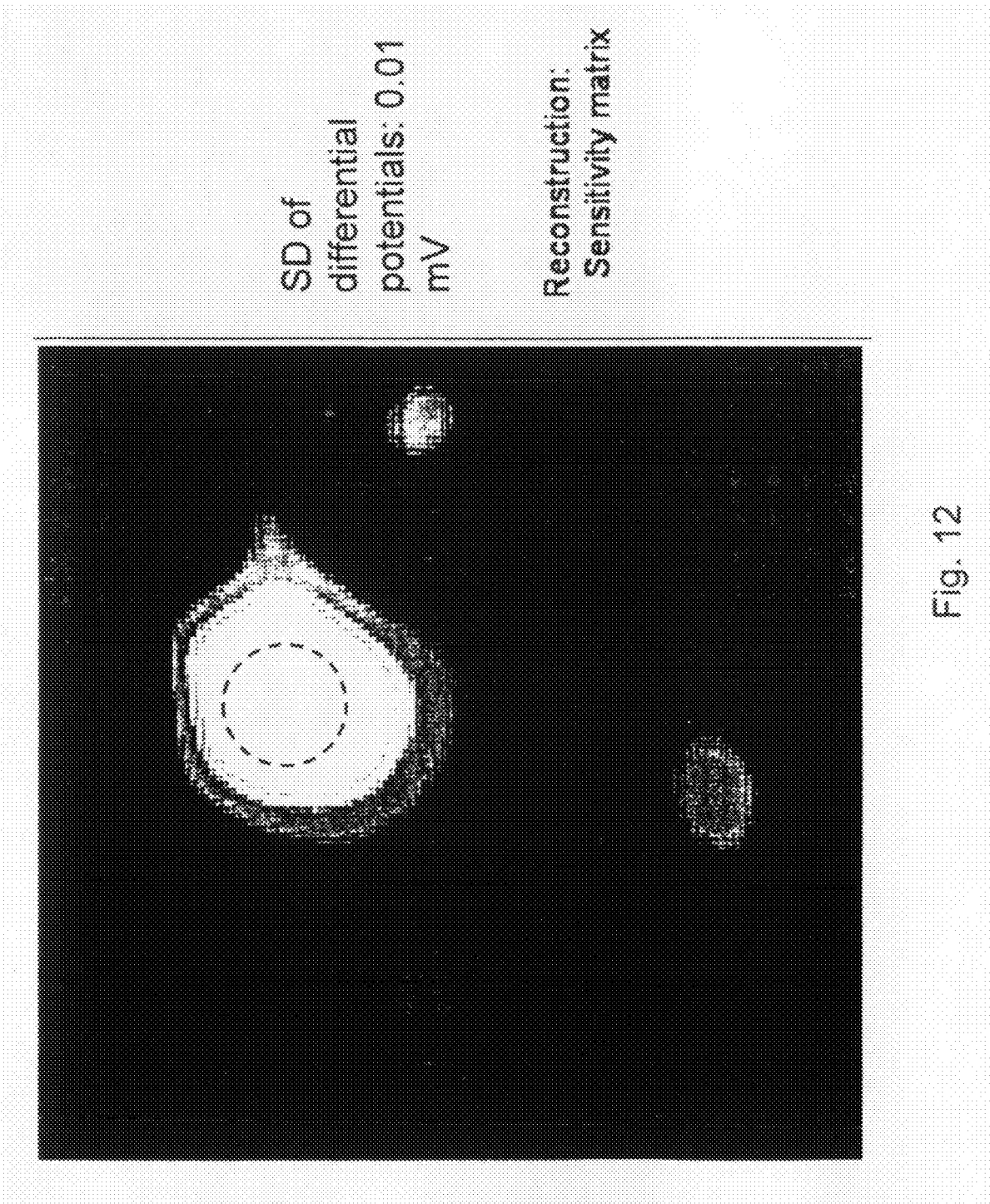

FIG. 12 shows the result of an image reconstruction using an adjacent configuration and a reconstruction algorithm based on the sensitivity matrix calculations for a finite element mesh model. This reconstruction algorithm is explained for example in Morucci J. P. et al., "A direct sensitivity matrix approach for fast reconstruction in electrical impedance tomography", Physiological Measurement, 15: A104-A114, 1994. The current source and intensity was the same as in FIG. 9, with the same system and cables, generating exactly the same background noise. Under the particular conditions tested, with a constant random noise across the electrodes, the algorithm resulted in better spatial resolution and it propagated less noise to the image than the back projection algorithm.

Figure 13:
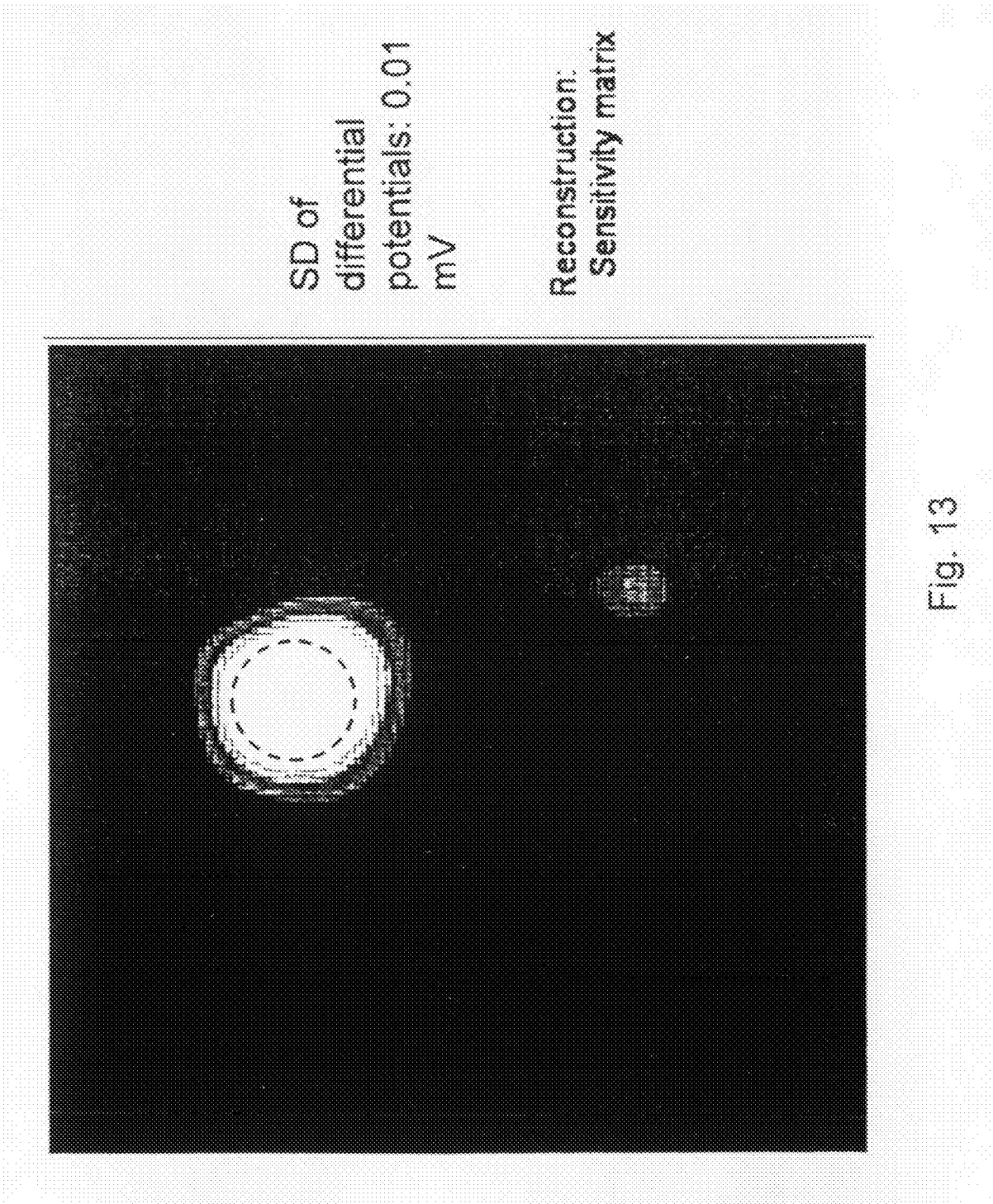

FIG. 13 shows the result of an image reconstruction using a configuration according to the invention with one electrode lying in between the current applying pairs/measuring pairs and a reconstruction algorithm based on the sensitivity matrix calculations for a finite element mesh model. Again, current source settings and background noise were kept constant like in FIG. 9. When compared to FIG. 12, image noise decreased and the spatial resolution improved. The reason for this improvement is the better signal-to-noise ratio in differential potential measurements, without loosing the major advantage of a differential potential system with current applying electrodes located comparatively close to each other, namely its high spatial frequency of excitation, leading to a greater number of independent measurements.

The invention claimed is:

1. Method for carrying out data collection on electrodes placed on a body for subsequent processing of an electrical impedance tomography image of a corresponding part of the body by means of a reconstruction algorithm, the method comprising the steps of:
   placing the electrodes on a peripheral line around the body;
   applying a current pattern from a current source to at least one pair of electrodes;
   measuring differential potentials between pairs of electrodes;
   selecting the pairs of electrodes so that at least one intermediate electrode lies in between each pair of electrodes for measuring the differential potentials;
   selecting the pairs of electrodes so that the at least one intermediate electrode is part of another pair of electrodes for measuring the differential potentials;
   using the differential potentials of one current pattern for the subsequent image processing from at least three different pairs of electrodes with no electrode used more than twice for each current pattern; and
   accounting for spatial overlap information in the data collection by the reconstruction algorithm.

2. Method according to claim 1, wherein the same number of electrodes lies in between each pair of electrodes for measuring a differential potential.

3. Method according to claim 1, wherein the same number of electrodes lies in between each pair of electrodes for applying a current.

4. Method according to claim 1, wherein for one current pattern each electrode on said peripheral line is used either for applying a current or for measuring differential potentials.

5. Method according to claim 1, wherein for one current pattern each electrode on said peripheral line is used for measuring differential potentials.

6. Method according to claim 5, wherein for one current pattern each electrode is used twice for measuring differential potentials.

7. Method according to claim 1, wherein a differential potential measurement is performed by measuring a first voltage of a first electrode with regard to the ground of the current source, measuring a second voltage of a second electrode with regard to the ground of the current source and subtracting the second voltage from the first voltage.

8. Method according to claim 1, wherein a balanced current source is used having a mid-point earthing as ground.

9. Method according to claim 1, wherein the electrodes are placed on at least one electrode unit.

10. Apparatus for carrying out data collection for an electrical impedance tomography image, comprising:

electrodes placed on a peripheral line around a body for processing of said electrical impedance tomography image of a corresponding part of the body by means of a reconstruction algorithm;

current source for applying a current pattern to at least one pair of electrodes;

measuring means for measuring differential potentials between pairs of electrodes using electrodes for the pairs of electrodes such that at least one intermediate electrode lies in between each pair of electrodes for measuring the differential potentials and the at least one intermediate electrode is part of another pair of electrodes for measuring the differential potentials, wherein the differential potentials of one current pattern for the subsequent image processing refer to at least three different pairs of electrodes and the measuring means uses no electrode more than twice for each current pattern; and computer means for implementing the reconstruction algorithm accounting for spatial overlap information in the data collection.

11. Apparatus according to claim 10, wherein the same number of electrodes lies in between each pair of electrodes for measuring a differential potential.

12. Apparatus according to one of the claim 10, wherein the same number of electrodes lies in between each pair of electrodes for applying a current.

13. Apparatus according to one of the claim 10, wherein for one current pattern each electrode on said peripheral line is used either for applying a current or for measuring differential potentials.

14. Apparatus according to one of the claim 10, wherein for one current pattern each electrode on said peripheral line is used for measuring differential potentials.

15. Apparatus according to claim 14, wherein for one current pattern each electrode is used twice for measuring differential potentials.

16. Apparatus according to one of the claim 10, wherein a differential potential measurement is performed by measuring a first voltage of a first electrode with regard to the ground of the current source, measuring a second voltage of a second electrode with regard to the ground of the current source and subtracting the second voltage from the first voltage.

17. Apparatus according to one of the claim 10, wherein a balanced current source is used having a mid-point earthing as ground.

18. Apparatus according to one of the claim 10, wherein the electrodes are placed on at least one electrode unit.

\* \* \* \* \*